United States Patent [19]

Fu

[11] Patent Number: 4,488,939

[45] Date of Patent: Dec. 18, 1984

[54] VAPOR CORROSION RATE MONITORING METHOD AND APPARATUS

[75] Inventor: John W. Fu, Monroeville, Pa.

[73] Assignee: Westinghouse Electric Corp., Pittsburgh, Pa.

[21] Appl. No.: 461,797

[22] Filed: Jan. 28, 1983

[51] Int. Cl.$^3$ ............................................. G01N 27/46
[52] U.S. Cl. .................................... 204/1 T; 204/404
[58] Field of Search ............................. 204/1 C, 404; 324/65 CR; 73/86

[56] References Cited

U.S. PATENT DOCUMENTS

| | | | |
|---|---|---|---|
| 3,599,090 | 8/1971 | Fitzpatrick et al. | 324/71 C |
| 3,633,099 | 1/1972 | Richman | 324/71 C |
| 3,924,175 | 12/1975 | Wilson | 324/30 R |
| 4,196,057 | 4/1980 | May et al. | 204/1 T |

OTHER PUBLICATIONS

E. C. French et al., "A Flush Mounted Probe For Instantaneous Corrosion Measurements In Gas Transmission Lines", *Materials Performance*, Jul. 1978, pp. 13–18.
F. Mansfeld et al., "Electrochemical Measurements of Time-of-Wetness and Atmospheric Corrosion Rates", *Corrosion–Nace*, vol. 33, pp. 13–16 (1977).
L. F. G. Williams et al., "iR Correction Part I. A Computerized Interrupt Method", *J. Electroanal. Chem.*, vol. 108, pp. 290–303 (1980).
F. Mansfeld, "Tafel Slopes And Corrosion Rates From Polarization Resistance Measurements", *Corrosion–Nace*, vol. 29, pp. 397–402 (1973).
M. Berthold et al., "Investigations of Corrosion with Measurement and Compensation of the Ohmic Drop", *Corrosion-Nace*, vol. 38, pp. 241–245 (1982).
J. W. Fu, "A Finite Element Analysis of Corrosion Cells", *Corrosion-Nace*, vol. 38, pp. 295–296 (1982).
J. W. Fu, "IR Voltage Correction in Electrochemical Atmospheric Corrosion Probes Using A Finite Element Calculation", paper presented at International Corrosion Forum, Apr. 1981, Toronto, Canada.

*Primary Examiner*—Aaron Weisstuch
*Attorney, Agent, or Firm*—C. M. Lorin

[57] ABSTRACT

A vapor corrosion rate monitoring probe having test, reference and auxiliary electrodes mounted flush on an electrically insulating body for exposure along a plane with a condensate of a corrosive vapor environment thereon, a front plate being mounted on said body a distance therefrom to define a crevice of predetermined characteristics in front of said exposed electrodes.

7 Claims, 5 Drawing Figures

VAPOR CORROSION RATE MONITORING METHOD AND APPARATUS

BACKGROUND OF THE INVENTION

The invention relates to corrosion monitoring in general, and more particularly to vapor corrosion monitoring. Corrosion under condensed vapors is a serious problem in steam turbines, pipe lines of natural gas, etc. Acid rains are also of concern. There is a need for vapor corrosion monitoring, e.g., continuous monitoring in situ of the corrosion rate in an environment of potentially corrosive vapor.

Corrosion rate measurements using electrochemical methods have been used for liquid corrosion. These involve electrochemical phenomena between a working electrode and a reference electrode with the assist of an auxiliary electrode. In these measurements the voltage drop (IR) along the potential measuring path must be corrected. The IR voltage drop is a troublesome problem in the use of electrochemical techniques for corrosion monitoring. See for instance: Lindsay F. G. Williams and Russell J. Taylor, "IR Correction: Part I A Computerized Interrupt Method"; "Part II Effect on Corrosion Monitoring", *J. Electroanal. Chem.* Vol. 108, pp. 290-316 (1980); Florian Mansfeld "Tafel Slopes and Corrosion Rates from Polarization Resistance Measurements" in *Corrosion-NACE,* Vol. 29, No. 10, October, 1973 pp. 397-402; Monika Berthold and Sigrun Herrmann, "Investigations of Corrosion with Measurement and Compensation of the Ohmic Drop", *Corrosion-NACE,* Vol. 38, No. 5., May 1982, pp 241-245.

This prior art, however, is concerned with corrosion rates with liquids. The situation is quite different when measuring corrosion rates due to a vapor, for instance for atmospheric corrosion monitoring.

IR voltage compensation in corrosion with vapor becomes a more serious problem in the measurement of electrochemical corrosion rate since there is a large electrolytic resistance between the working and the reference electrode. As a result the IR voltages due to the reference electrode being located in the path of significant current flowing between working and counter electrodes affect the measurement considerably. The IR portion of the voltage measured by the reference electrode is due to an IR voltage drop that appears when current flows in a resistive electrolyte. This resistive electrolyte is due to vapor condensation in a very thin film, thus of very high resistance. For accurate estimates of corrosion rate, this IR contribution must be separated from the true potential change at the working electrode surface. If the IR voltage drops are not compensated for in electrochemical corrosion rate monitoring, the corrosion rate calculation can seriously underestimate the true corrosion rate of the working electrode. The compensation for IR voltage drops is particularly important for linear polarization methods because the small polarization potentials ($\pm 10$ mV) introduce a high sensitivity to even a few millivolts of uncompensated IR voltage in the corrosion rate calculation.

This IR voltage drop constitutes an especially serious problem in atmospheric corrosion probes since the corrosive environment is a thin condensed film which has high resistance due to its thinness. Therefore, it must be compensated for.

Thus, this IR voltage drop is a major problem limiting the use of the linear polarization corrosion rate measurement in atmospheric corrosion monitoring. Unfortunately, the IR voltage is not only a function of the resistivity of the environment, is also a function of the resistance of the current path. The latter varies with the location of the reference electrode and also depends upon the geometric shape of the corrosive environment. It is known to use a computer in order to ascertain the relation between a particular geometry and the resistance involved in the IR voltage drop. See, for instance paper by John W. Fu entitled "A Finite Element Analysis of Corrosion Cells" In *Corrosion,* Vol. 38, No. 5, pp. 295-296, May 1982. This paper is hereby incorporated by reference. Due to the complex dependence of IR voltage drop on these parameters, no simple mathematical calculation has been available for IR voltage drop compensation in potential measurements during an electrochemical corrosion rate measurement. To overcome the difficulty, a finite element method for calculating IR voltage drop in corrosion cells has been proposed as explained by John W. Fu in a paper entitled "IR Voltage Correction in Electrochemical Atmospheric Corrosion Probes Using a Finite Element Calculation", presented at the International Corrosion Forum Apr. 6-10, 1981, Toronto, Ontario, Canada. The IR voltage is calculated using numerical solutions of the governing partial differential equations for corrosion cells. It is also proposed in that paper to model the geometric shape of the corrosive environment by an assembly of small elements called an element mesh. The electrode surfaces are modeled by the surfaces of elements at the boundary of an element mesh. The potential at each element location is generated by the numerical solution of the governing differential equations. The difference in potential between the reference electrode surface and the working electrode surface is the IR voltage drop for a set of assumed conditions which include the resistivity of the corrosive environment, the total current flow between the counter and the working electrode and the locations of each of the three electrodes.

Using this method, it has been possible to examine the IR voltage drop as a function of various parameters, thus aiding in the design of the probe that produces the lowest IR voltage drop. Furthermore, for a given corrosion probe design, an IR voltage drop calibration curve (as a function of current flow and resistivity of the corrosive environment) can be generated to compensate the IR voltage drop component in subsequent potential measurements. This indirect and theoretical approach, however, does not provide true geometrical characteristics for an in situ vapor corrosion rate measurement.

On account of the very thin film buildup at the juncture between the corrodent vapor and the exposed surface of the corroding metal, corrosion rate measurements have been proposed to be made in situ within a pipe carrying natural gas with the assist of a planar probe embodying working and reference electrodes, as well as an auxiliary electrode used for the determination of the IR voltage drop. See, for instance, U.S. Pat. No. 4,196,057, and the article by Eddie C. French and Paul B. Eaton entitled "A Flush Mounted Probe for Instantaneous Corrosion Measurements in Gas Transmission Lines", in *Materials Performance,* pp. 13-18, July 1978.

A general treatment of atmospheric corrosion rates is also to be found in the article entitled "Electrochemical Measurements of Time Wetness and Atmospheric Corrosion Rates" by F. Mansfeld and J. V. Kenkel in *Corro-* sion-*NACE*, Vol. No. 33, January 1977, pp. 13–16, and in the appendent reference listing.

SUMMARY OF THE INVENTION

The present invention resides in an improved vapor corrosion rate monitoring apparatus comprising a main planar body of electrically insulating material having a front face traversed by a test electrode, a reference electrode and two auxiliary electrodes straddling said test electrode; a plate member of electrically insulating material facing said front face a distance therefrom to define a crevice therebetween; potentiostat means associated with said back face and connected with said test, reference and auxiliary electrodes for deriving potential representative signals between said test and reference electrodes in a test mode and current representative signals between said two auxiliary electrodes in a calibration mode; and means for combining said potential and current representative signals to derive an indication of vapor corrosion within said device.

DETAILED DESCRIPTION OF THE INVENTION

Figure 1:
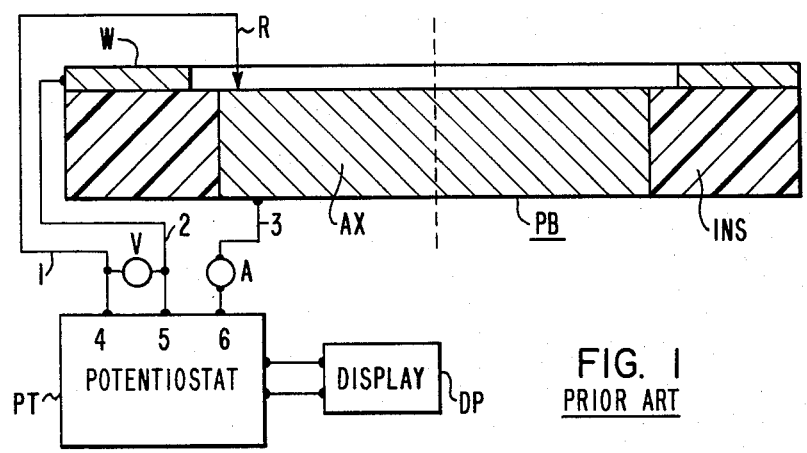
FIG. 1 illustrates prior art probe design and circuitry for monitoring vapor corrosion rate.

FIG. 1 is taken from the afore-mentioned paper entitled "IR Voltage Correction in Electrochemical Atmospheric Corrosion Probes Using a Finite Element Calculation" by John W. Fu, presented at the International Corrosion Forum of Apr. 6–10, 1981 in Toronto, Ontario, Canada. This publication by John W. Fu is hereby incorporated by reference for the purpose of the instant disclosure.

In a vapor environment the probe PB includes a disc-shape conductive body AX serving as an auxiliary electrode. Electrode AX is surrounded by an insulative ring INS. On top of ring INS is mounted a ring-shaped working electrode W of inner diameter somewhat larger than the diameter of the auxiliary electrode AX. In other words, insulating ring INS electrically isolates electrode AX from electrode W. A reference electrode R of pencil shape is positioned so as to be close to the upper surface of electrode AX. The ring electrode W has a small transversal dimension so as to define on the upper face of electrode AX a very thin volume. Typically, electrode W has an internal diameter of one centimeter, and a thinness of 0.0064 cm. Corrosion by the vapor in the environment is characterized by a thin film of condensate formed on the exposed surface of the probe within the confines of that volume of $(\pi/4 \times 1 \times 0.0064)$ cm$^3$. Materials to be used in the probe PB typically are: stainless steel for electrode AX and for ring electrode W; platinum for the reference electrode R; Teflon for insulator ring INS.

In accordance with the IR compensation technique used for corrosion rate measurement with liquids, the reference electrode R and the working electrode W are used to detect a potential difference $V_m$ therebetween. $V_m$ is derived with a voltmeter between conductors 1 and 2 from R and W, respectively, to opposite inputs 4 and 5 of a potentiostat PT. An AC source is applied between terminals 5 and 6 of the potentiostat and lines 2, 3 to a path defined between electrode W and electrode AX used as a counter-electrode. The path is through the condensate, or electrolyte, laying on the surface of the probe therebetween. An ammeter A inserted in line 3 provides an indication of the current flowing in this path. The afore-mentioned reference on IR correction by F. G. Williams and R. I. Taylor dated 1979, the reference of M. Berthold and S. Herrmann dated 1982 on compensation of the ohmic drop, and the reference of F. Mansfeld on polarization measurements dated 1973, are hereby incorporated by reference for the purpose of disclosing herein how a reference electrode like R, a working electrode like W and a counter electrode like AX can be used for the measurement of corrosion rates with a potentiostat using IR compensation. The potentiostat PT establishes a calibration mode for which the voltage drop is measured and a test mode for which $V_m$ the potential between lines 1 and 2 is known. The true value V due exclusively to the condensate film resistivity between electrodes R and W is $V = V_m - IR$. For various values of V and I a curve can be plotted having a slope which is the corrosion rate sought with the potentiostat. An equipment DP is associated with the potentiostat to provide the information on display. The IR display depends upon I measured and R the path resistance through the condensate. However, the resistance R not only depends upon the resistivity $\rho$ of the condensate, but also upon the geometry G in the corrosive environment of the vapor. It also depends, like the current I, upon the position of the reference electrode. Due to such complex dependence on these parameters, no simple mathematical calculation of the IR voltage has been possible and, therefore, no true IR voltage compensation in potential measurements V during electrochemical corrosion rate testing could be derived from a vapor corrosion cell such as shown in FIG. 1.

As explained in the afore-mentioned Fu paper, an IR voltage calculation method has been attempted based on the numerical solution of the partial differential equations governing the geometry of a corrosion cell such as shown in FIG. 1.

To this effect, the geometric shape of the corrosive environment has been molded with an assembly of small elements associated to form a regular mesh. The electrode surfaces are defined by the surfaces supported by the elements at the boundary. The potential at each element location is defined by the numerical solution of the governing equations. The potential difference between the reference electrode surface and the working electrode W is the IR voltage for a set of assumed conditions including: the resistivity of the corrosion environment; the geometric shape due to the mesh-like model for the environment; the total current flow between the auxiliary (or counter) electrode and the working electrode; the locations of each of the three electrodes.

Figure 2:
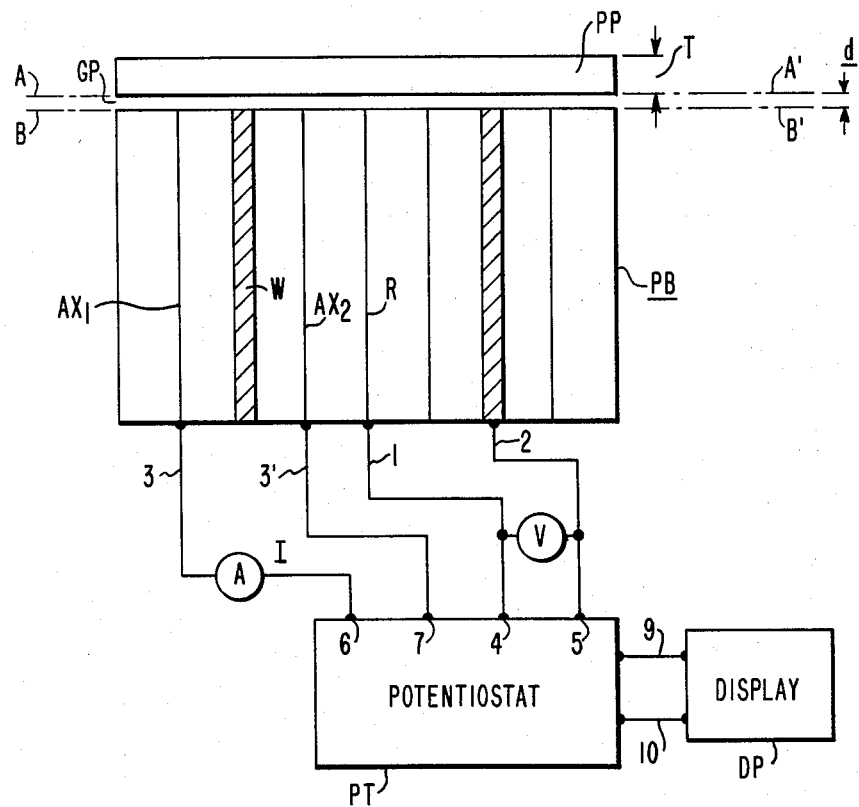
FIG. 2 shows in cross-section one embodiment of the probe according to the present invention, and the associated circuitry for monitoring vapor corrosion rate.

The present invention is a departure from the proposal in the Fu paper incorporated by reference. It is also a practical solution in order to create about the exposed surface of the probe an environment of constant and well-defined geometry. Referring to FIG. 2, the probe PB (typically of 0.9525 cm in diameter) according to the present invention appears to possess, on top of the face exposed to corrosive environment, a front plate PP (typically of thickness T=0.3175 cm) defining therebetween a crevice, or gap GP of sufficient thickness as to allow the formation of a film of electrolyte by condensation from the surrounding vapor (typically GP=0.0076 cm). The central electrode in the body of the probe is the reference electrode R. The working electrode W is concentrically disposed at a selected radial distance (typically at 0.635 cm from the reference electrode R). Two auxiliary electrodes are provided $AX_1$, $AX_2$ which are concentrically disposed about the working electrode W, one $AX_1$ to the outside (typically at a distance 0.9525 cm from R), the other $AX_2$ inside (typically at 0.3175 cm from R) between the reference R and the working electrode W. Circuitry similar to that of FIG. 1 is used, connected to the electrodes where they are flush on lower surface of the probe. Lines 1 and 2 from terminals 4 and 5 of the potentiostat PT are connected to reference electrode R and working electrode W, respectively. In accordance with the present invention the resistive path measured during calibration between terminals 6 and 7 of the potentiostat is established by lines 3 and 3' between the two auxiliary electrodes $AX_1$ and $AX_2$, respectively. All electrodes are flush with the upper face of the main body of the probe, thus on one side of the crevice.

The plane A—A' of the lower face of the front plate PP and the plane B—B' of the upper face of the main body of the probe from a gap GP of transversal dimension d. As explained in the afore-mentioned publications incorporated by reference, the voltage measured during testing between lines 1 and 2 is compensated by the IR voltage drop between lines 3 and 3', on account of the current I measured during calibration with the ammeter A of line 3. Since the probe of FIG. 2, however, has a constant geometry in any vapor environment, a true measure of the resistivity $\rho$ in situ for a given current I is made possible from the known resistance.

Materials for the various parts of the probe PB in FIG. 2 typically are: platinum for electrode R; for the working electrode W: stainless steel or any low alloy carbon-steel metal, for the auxiliary electrodes $AX_1$ and $AX_2$: platinum coated titanium. The test, or working electrode W may also be made of a copper alloy. The body of the probe PB, and the front plate PP consist of an electrical insulator material. It is important, though, for the opposing faces of the crevice that the material not be hydrophobic, since condensation from the surrounding corrosive vapor should be able to form a film within the crevice. A preferred material for the body is alumina.

More generally, recommended materials are as follows:

For the main body of the probe PB and the front plate PP: alumina, or other material which is nonconductive and nonhydrophobic;

For the reference electrode R: the same as for test electrode W, or even a more stable material such as platinum;

For the auxiliary electrodes $AX_1$, $AX_2$, platinum or platinized titanium.

Figure 3:
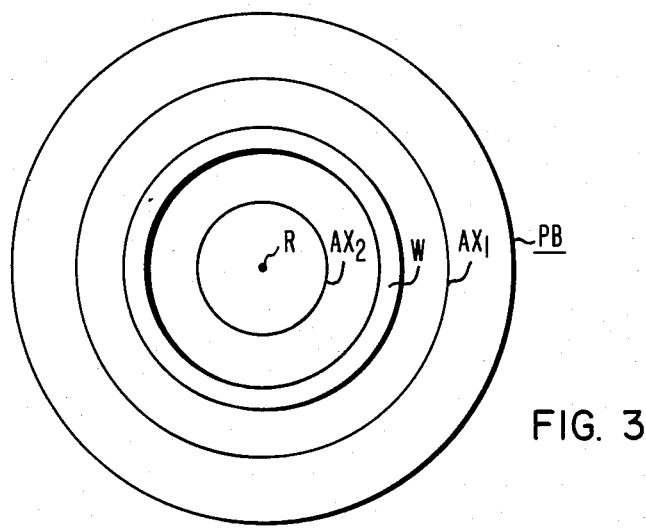
FIG. 3 is a top view of the exposed face of the probe of FIG. 2 with the operative electrodes flush on that face.

FIG. 3 is a top view of the probe as seen above plane B—B', the plane of the electrodes.

The probe according to the invention operates as follows:

In a calibration mode selected by potentiostat PT, an AC current I is passed between auxiliary electrodes $AX_1$, $AX_2$ (lines 3, 3'). As a result, the system ascertains the resistance R of the path including the electrolyte, or condensate, in the crevice. From the geometrical characteristics involved with such a path and the value of R, the resistivity $\rho$ of the electrolyte is determined.

In a testing mode, the voltage V between lines 1 and 2 from the potentiostat is initially ascertained. Then, a current I is passed between line 3 (or 3'), e.g. between one of the auxiliary electrodes and the test, or working electrode W. The current I is determined and the decrease $\Delta Vm$ of voltage between lines 1 and 2 is derived. Using the value of the resistivity determined during calibration and applying the geometrical constant characterizing the current path with the probe and its crevice GP, the resistance R is determined. Compensation by the polarization resistance technique leads to the true value $\Delta V = \Delta Vm - RI$. Referring to the two afore-mentioned instances where (1) $\rho$ is derived from the ascertained resistance R, and (2) in the test mode R is derived from the resistivity determined during calibration, in each instance a computation is effected based on a modeling technique such as illustrated in the article by J. Fu in *Corrosion*, Vol 38, No. 5, pp. 295-296 (May 1982) which is incorporated by reference.

Figure 4:
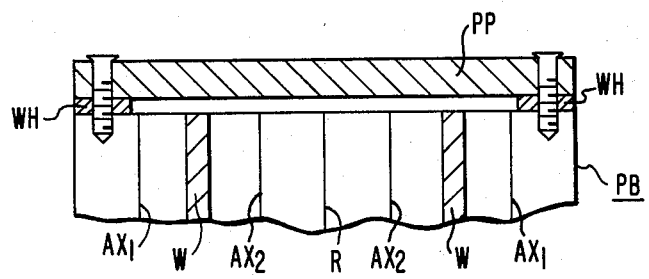
FIG. 4 is illustrative of one way of mounting the front plate of the probe of FIG. 2.

FIG. 4 illustrates a mode of fixation for the front plate PP on the top of the probe main body. To this effect, washers WH are interposed to fix the size of the gap GP of the crevice, and screws are placed across the journalled plate PP at various locations to the periphery and driven into the body of the probe beyond the washers WH.

Figure 5:
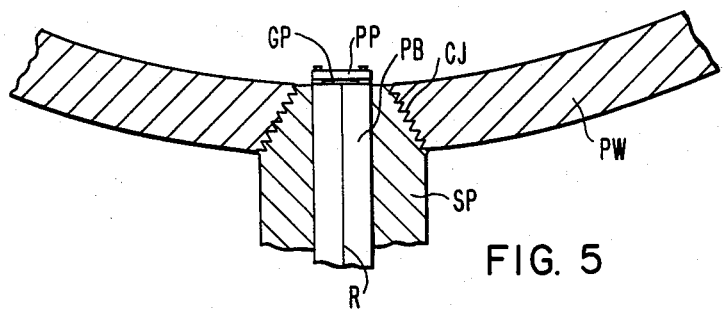
FIG. 5 is illustrative of the application of the probe of FIG. 2 to measurement of corrosion rate within the wall of a natural gas pipe.

FIG. 5 shows the probe applied to a natural gas pipe. The probe PB is mounted within a support SP having a conax type of fitting with the wall of the pipe PW. The probe ends flush with the inner surface of the pipe wall, except for the front plate PP defining the crevice. Natural gas flowing in the pipe will cause condensation within the crevice GP of the probe. Testing and calibration will be carried out from the outside. The probe according to the present invention is, thus, used in a manner similar to the flush mounted probe described by E. C. French and P. E. Eaton in the article "A Flush Mounted Probe for Instantaneous Corrosion Measurements in Gas Transmission Lines", *Materials Performance*, (July 1978) pp. 13–18. The superiority of the probe according to the present invention, however, is well understood from the preceding descriptive considerations.

Probes for the measurement of crevice corrosion have been designed which exhibit a crevice in the probe. See for instance U.S. Pat. Nos. 3,633,099 and 3,599,090. However, these probes are not designed for vapor corrosion rate measurement. The first patent involves liquid admitted within the crevice; the second patent does not involve an electrochemical method of corrosion measurement.

The disc-shape probe PB of FIGS. 1 and 2 is merely illustrative of the preferred embodiment of the invention. The probe could be made rectangular, and the electrodes could be disposed in parallel planes rather then being concentric. Changes can be made as a matter of design and with the results of experience, as well as in accordance with practical considerations under the teachings of the present invention.

I claim:

1. A vapor corrosion rate monitoring apparatus including a probe comprising:
    a main planar body having a front face traversed by a test electrode, a reference electrode and two auxiliary electrodes straddling said test electrode;
    a plate member facing said front face a distance therefrom to define a crevice therebetween;
    with said main planar body and plate member being of electrically insulating material;
    the apparatus further including:
    potentiostat means connected with said test, reference and auxiliary electrodes for deriving potential representative signals between said test and reference electrodes in a test mode and current representative signals between said auxiliary electrodes in a calibration mode; and
    means for combining said potential and current signals to derive an indication of vapor corrosion rate within said crevice.

2. The apparatus of claim 1 with said main planar body and plate member being made of alumina.

3. The apparatus of claim 1 with the material of said test electrode being selected from the group of metals including carbon steel, stainless steel, copper alloy.

4. The apparatus of claim 1 with the material of said reference electrode being selected from the group of metals including carbon steel, stainless steel, copper alloy, platinum.

5. The apparatus of claim 3 or 4 with said auxiliary electrodes being made of platinum.

6. The apparatus of claim 5 with said auxiliary electrodes being made of platinized titanium.

7. A method of measuring corrosion rate in condensed vapor by the electrochemical polarization technique involving: a probe including a main planar body of electrically insulating material having a front face and a reference electrode, a test electrode and two auxiliary electrodes straddling said test electrode, said electrodes being embedded in said planar body up to said front face; a plate member of electrically insulating material facing said front face a distance therefrom to define a crevice there-between; said probe being exposed in said vapor to form a film of vapor condensate in said crevice; the method comprising the steps of:
    in a calibration mode applying a first AC current of magnitude I through a first current path between said two auxiliary electrodes, measuring the first path resistance R through the condensed vapor and computing from said resistance R the resistivity of said vapor condensate;
    in a testing mode applying a second AC current of magnitude I' through a second current path between one of said auxiliary electrodes and said test electrode, concurrently measuring a potential decrement between said reference electrode and said test electrode, computing the resistance R' in said second path from said computed resistivity, determining a voltage drop I'R' with said computed resistance R' and compensating said potential decrement with said voltage drop thereby to establish a corrosion rate value.

* * * * *